US008097742B2

(12) United States Patent
Ying et al.

(10) Patent No.: US 8,097,742 B2
(45) Date of Patent: Jan. 17, 2012

(54) WATER-SOLUBLE, SURFACE-FUNCTIONALIZED NANOPARTICLE FOR BIOCONJUGATION VIA UNIVERSAL SILANE COUPLING

(75) Inventors: Jackie Y. Ying, Singapore (SG); Nikhil R. Jana, Singapore (SG); Yuangang Zheng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1155 days.

(21) Appl. No.: 11/795,639

(22) PCT Filed: Jan. 20, 2005

(86) PCT No.: PCT/SG2005/000016
§ 371 (c)(1),
(2), (4) Date: Jul. 18, 2007

(87) PCT Pub. No.: WO2006/080895
PCT Pub. Date: Aug. 3, 2006

(65) Prior Publication Data
US 2008/0045736 A1     Feb. 21, 2008

(51) Int. Cl.
*C07F 7/08* (2006.01)
(52) U.S. Cl. .................................................. 556/425
(58) Field of Classification Search .................. 556/425
See application file for complete search history.

(56) References Cited

U.S. PATENT DOCUMENTS

| | | | |
|---|---|---|---|
| 6,207,392 B1 | 3/2001 | Weiss et al. | |
| 6,251,303 B1 | 6/2001 | Bawendi et al. | |
| 6,319,426 B1 | 11/2001 | Bawendi et al. | |
| 7,410,810 B2 * | 8/2008 | Bohmann et al. | 436/524 |
| 2003/0083401 A1 | 5/2003 | Schneider et al. | |
| 2003/0180780 A1 * | 9/2003 | Feng et al. | 435/6 |
| 2004/0033270 A1 | 2/2004 | Kropf et al. | |
| 2004/0033345 A1 | 2/2004 | Dubertret et al. | |
| 2004/0072373 A1 * | 4/2004 | Lin et al. | 436/526 |

FOREIGN PATENT DOCUMENTS

| WO | WO 2004/011672 | * | 2/2004 |
|---|---|---|---|
| WO | WO 2004/108116 A2 | | 12/2004 |

OTHER PUBLICATIONS

Abdullah et al., "Generating Blue and Red Luminescence from ZnO/Poly(ethylene glycol) Nanocomposites Prepared Using an in-Situ Method," *Advanced Functional Materials* 13(10):800-804, 2003.
Alivisatos, "The use of nanocrystals in biological detection," *Nature Biotechnology* 22(1):47-52, 2004.
Buining et al., "Preparation of Functional Silane-Stabilized Gold Colloids in the (Sub)nanometer Size Range," *Langmuir* 13:3921-3926, 1997.
Cao et al., "Nanoparticles with Raman Spectroscopic Fingerprints for DNA and RNA Detection," *Science* 297:1536-1540, 2002.
Cao et al., "Preparation and radiolabeling of surface-modified magnetic nanoparticles with rhenium-188 for magnetic targeted radiotherapy," *Journal of Magnetism and Magnetic Materials* 277:165-174, 2004.
Chan et al., "Luminescent quantum dots for multiplexed biological detection and imaging," *Current Opinion in biotechnology* 13:40-46, 2002.
Chen et al., "Tissue Selective Affinity Targeting Using the Avidin-Biotin System," *Drug Development Research* 50:258-271, 2000.
Daniel et al., "Gold Nanoparticles: Assembly, Supramolecular Chemistry, Quantum,-Size-Related Properties, and Applications toward Biology, Catalysis and Nanotechnolgy," *Chemical Reviews* 104:293-346, 2004.
Elghanian et al., "Selective Colorimetric Detection of Polynucleotides Based on the Distance-Dependent Optical Properties of Gold Nanoparticles," *Science* 277:1078-1081, 1997.
Feng et al., "Functionalized Europium Oxide Nanoparticles Used as a Fluorescent Label in an Immunoassay for Atrazine," *Analytical Chemistry* 75(19):5282-5286, 2003.
Gerion et al., "Synthesis and Properties of Biocompatible Water-Soluble Silica-Coated CdSe/ZnS Semiconductor Quantum Dots," *J. Phys. Chem. B* 105:8861-8871, 2001.
Guo et al., "Conjugation Chemistry and Bioapplications of Semiconductor Box Nanocrystals Prepared via Dendrimer Bridging," *Chem. Mater.* 15(16):3125-3133, 2003.
He et al., "A Novel Method for Efficient Gene Delivery Using Amino-Modified Silica Coated Magnetic Nanoparticles," *Rev. Adv. Mater. Sci.* 5:375-380, 2003.
Hyeon et al., "Synthesis of Highly Crystalline and Monodisperse Maghemite Nanocrystallites without a Size-Selection Process," *J. Am. Chem. Soc.* 123(51):12798-12801, 2001.
Jana et al., "Single-Phase and Gram-Scale Routes toward Nearly Monodisperse Au and Other Noble Metal Nanocrystals," *J. Am. Chem. Soc.* 125(47):14280-14281, 2003.
Jana et al., "Size- and Shape-Controlled Magnetic (Cr, Mn, Fe, Co, Ni) Oxide Nanocrystals via a Simple and General Approach," *Chem. Mater.* 16(20):3931-3935, 2004.

(Continued)

*Primary Examiner* — Shailendra Kumar
(74) *Attorney, Agent, or Firm* — Klarquist Sparkman, LLP

(57) ABSTRACT

The invention provides a process for the preparation of a surface-functionalized nanoparticle comprising: (a) reacting a nanoparticle with a functionalized silane and a base in a substantially non-aqueous solvent to obtain a partially conjugated silanated nanoparticle, wherein the functionalized silane and the base are present in relative amounts such that said functionalized silane undergoes substantially only a single hydrolysis reaction; (b) reacting the partially conjugated silanated nanoparticle formed in step (a) with a base in a solvent in which the partially conjugated silanated nanoparticle is substantially insoluble and in which the base is substantially soluble. The invention also provides a surface-functionalized nanoparticle prepared therefrom and a bioconjugate comprising said a surface-functionalized nanoparticle.

25 Claims, 9 Drawing Sheets

OTHER PUBLICATIONS

Kim et al., "Near-infrared fluorescent type II quantum dots for sentinel lymph node mapping," *Nature Biotechnology* 22(1):93-97, 2004.

Kneipp et al., "Ultrasensitive Chemical Analysis by raman Spectroscopy," *Chem. Rev.* 99(10):2957-2975, 1999.

Kohler et al., "A Bifunctional Poly(ethylene glycol) Silane Immobilized on Metallic Oxide-Based Nanoparticles for Conjugation with Cell Targeting Agents," *J. Am. Chem. Soc.* 126(23):7206-7211, 2004.

Larson et al., "Water-Soluble Quantum Dots for Multiphoton Fluorescence Imaging in Vivo," *Science* 300:1434-1436, 2003.

LaVan et al., "Small-scale systems for in vivo drug delivery," *Nature Biotechnology* 21(10):1184-1191, 2003.

Lingerfelt et al., "Preparation of Quantum Dot—Biotin Conjugates and Their Use in Immunochromatography Assays," *Anal. Chem.* 75(16):4043-4049, 2003.

Liu et al., "Synthesis of amino-silane modified superparamagnetic silica supports and their use for protein immobilization," *Colloids and Surfaces A: Physiochem Eng. Aspects* 238:127-131, 2004.

Liz-Marzán et al., "The Assembly of Coated Nanocrystals," *J. Phys. Chem. B* 107(30):7312-7326, 2003.

Meulenkamp, "Synthesis and Growth of ZnO Nanoparticles," *J. Phys. Chem. B* 102(29):5566-5572, 1998.

Murray et al., "Synthesis and Characterization of Nearly Monodisperse CdE (E—S, Se, Te) Semiconductor Nonocrystallites," *J. Am. Chem. Soc.* 115(19):8706-8715, 1993.

Nam et al., "Nanoparticle-Based Bio-Bar Codes for the Ultrasensitive Detection of Proteins," *Science* 301:1884-1886, 2003.

Osaki et al., "A Quantum Dot Conjugated Sugar Ball and Its Cellular Uptake. On the Size Effects of Endocytosis in the Subviral Region," *J. Am. Chem. Soc.* 126(21):6520-6521, 2004.

Parvin et al., "Synthesis and magnetic properties of monodisperse $Fe_3O_4$ nanoparticles," *Journal of Applied Physics* 95(11):7121-7123, 2004.

Pellegrino et al., "Hydrophobic Nanocrystals Coated with an Amphiphilic Polymer Shell: A General Route to Water Soluble Nanocrystals," *Nano Letters* 4(4):703-707, 2004.

Peng et al., "Formation of High-Quality CdTe, CdSe, and CdS Nanocrystals Using CdO as Precursor," *J. Am. Chem. Soc.* 123(1):183-184, 2001.

Riegler et al., "Visualizing the Self-Assembly of Tubulin with Luminescent Nanorods," *Journal of Nanoscience and Nanotechnology* 3(5):380-385, 2003.

Schroedter et al., "Biofunctionalization of Silica-Coated CdTe and Gold Nanocrystals," *Nano Letters* 2(12):1363-1367, 2002.

Schroedter et al., "Ligand Design and Bioconjugation of Colloidal Gold Nanoparticles," *Angew. Chem. Int. Ed.* 41(17):3218-3221, 2002.

Sun et al., "Monodisperse FePt Nanoparticles and Ferromagnetic FePt Nanocrystal Superlattices," *Science* 287:1989-1992, 2000.

Sung et al., "Synthesis of Monofunctionalzied Gold Nanoparticles by Fmoc Solid-Phase Reactions," *J. Am. Chem. Soc.* 126(16):5064-5065, 2004.

Tiefenauer et al., "Antibody-Magnetite Nanoparticles: In Vitro Characterization of a Potential Tumor-Specific Contrast Agent for Magnetic Resonance Imaging," *Bioconjugates Chem.* 4(5):347-352, 1993.

Tkachenko et al., "Multifunctional Gold Nanoparaticles—Peptide Complexes for Nuclear Targeting," *J. Am. Chem. Soc.* 125(16):4700-4701, 2003.

Ulman, "Formation and Structure of Self-Assembled Monolayers," *Chemical Reviews* 96(4):1533-1554, 1996.

Wang et al., "Determination of conjugation efficiency of antibodies and proteins to the superparamagnetic iron oxide nanoparticles by capillary electrophoresis with laser-induced fluorescence detection," *Journal of Nanoparticle Research* 5:137-146, 2003.

Weber et al., "Structural Origins of High-Affinity Biotin Binding to Streptavidin," *Science* 243:85-88, 1989.

West et al., "Engineered Nanomaterials for Biophotonics Applications: Improving Sensing, Imaging, and Therapeutics," *Annu. Rev. Biomed. Eng.* 5:285-292, 2003.

Wilchek et al.., "The Avidin—Biotin Complex in Bioanalytical Applications," *Analytical Biochemistry* 171:1-32, 1988.

Zhang et al., "Surface modification of superparamagnetic magnetite nanoparticles and their intracellular uptake," *Biomaterials* 23:1553-1561, 2002.

* cited by examiner

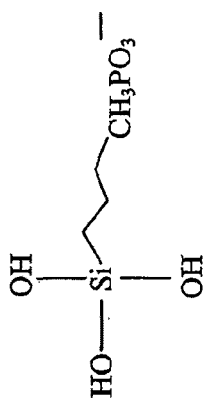
FIG. 3A
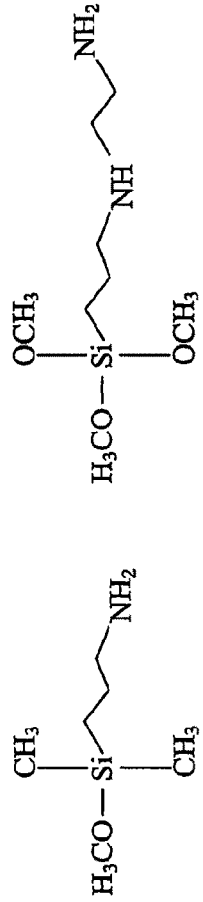
FIG. 3B
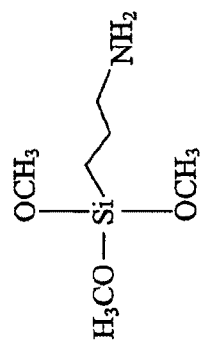
FIG. 3C
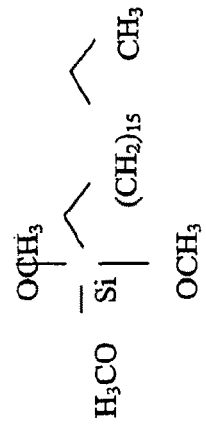
FIG. 3D
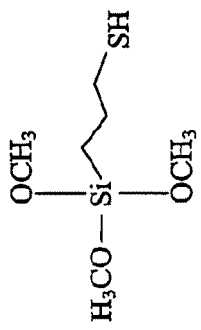

WATER-SOLUBLE, SURFACE-FUNCTIONALIZED NANOPARTICLE FOR BIOCONJUGATION VIA UNIVERSAL SILANE COUPLING

CROSS REFERENCE TO RELATED APPLICATIONS

This is the U.S. National Stage of International Application No. PCT/SG2005/000016, filed Jan. 20, 2005, which was published in English under PCT Article 21(2), which is incorporated herein in its entirety.

FIELD OF THE INVENTION

This invention relates to a process for the preparation of a surface-functionalized nanoparticle, to the surface-functionalized nanoparticle prepared therefrom, and to a bioconjugate comprising the surface-functionalized nanoparticle.

BACKGROUND OF THE INVENTION

Nanoparticles of 1-100 nm have broad applications in biology, such as in labelling, imaging, drug delivery, separation and optical sensing. The size of nanoparticles plays an important role in determining their properties as well as their effectiveness in bioapplications. The synthesis of monodisperse nanoparticles is critical to the tailoring and optimization of size-dependent characteristics.

Nanoparticles also require suitable surface functional groups in order to conjugate with biomolecules. Most biomolecules have carboxylic acid, primary amine, alcohol, phosphate, or thiol groups, and nanoparticles that are functionalized with primary amines, carboxylic acids and thiol surface groups can be covalently conjugated with biomolecules via amide, disulfide and ester bonds.

Many methods are currently available for nanoparticle synthesis. Most synthetic approaches are based on organic solvent routes where particles are coated with hydrophobic/lipophilic organic stabilizer molecules. The nanoparticles as synthesized cannot be used directly for biofunctionalization/bioapplication because they are insoluble in water, they do not have required functional groups for bioconjugation, and/or they are unstable toward various processing steps for bioapplications.

Currently, several strategies are available to solve these problems, for example by exchanging the original stabilizer with surfactant/ligand molecules or polymers, silanization, and dendron bridging. The key issue is to deal with the sensitive surface chemistry of the nanoparticles, and the colloidal stability of the nanoparticles in aqueous phase. Ligand-exchanged nanoparticles are less stable and often lead to irreversible aggregates as the nanoparticles lose their organic shells. To solve this problem, ligand-exchange followed by cross-coupling is used to provide covalent bridging surrounding the particles. Silanization and dendron bridging are unique alternative schemes to generate covalent bridging of stabilizer shell surrounding the nanoparticle. Using this approach, stable quantum dot and metallic nanoparticle dispersions can be prepared. However, these approaches often produce water-insoluble nanoparticles, because of interparticle bridging.

BRIEF SUMMARY OF THE INVENTION

In one aspect, the present invention provides a process for the preparation of a surface-functionalized nanoparticle comprising:

(a) reacting a nanoparticle with a functionalized silane and a base in a substantially non-aqueous solvent to obtain a partially conjugated silanated nanoparticle, wherein the functionalized silane and the base are present in relative amounts such that said functionalized silane undergoes substantially only a single hydrolysis reaction;

(b) reacting the partially conjugated silanated nanoparticle formed in step (a) with a base in a solvent in which the partially conjugated silanated nanoparticle is substantially insoluble and in which the base is substantially soluble.

In further aspects, the present invention provides a surface-functionalized nanoparticle prepared by the process described herein, and a bioconjugate comprising said surface-functionalized nanoparticle.

BRIEF DESCRIPTION OF THE DRAWINGS

Embodiments of the invention will be discussed with reference to the following Figures:

FIG. 3 shows chemical structures of various silanes that can be utilized to prepare a surface-functionalized nanoparticle.

DETAILED DESCRIPTION OF THE INVENTION

Figure 1A:
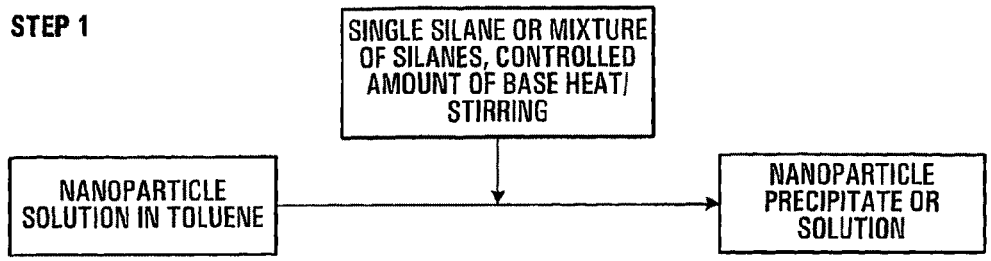
FIG. 1 is a flow chart illustrating a two-step silane conjugation on the surface of a nanoparticle.
Figure 1B:
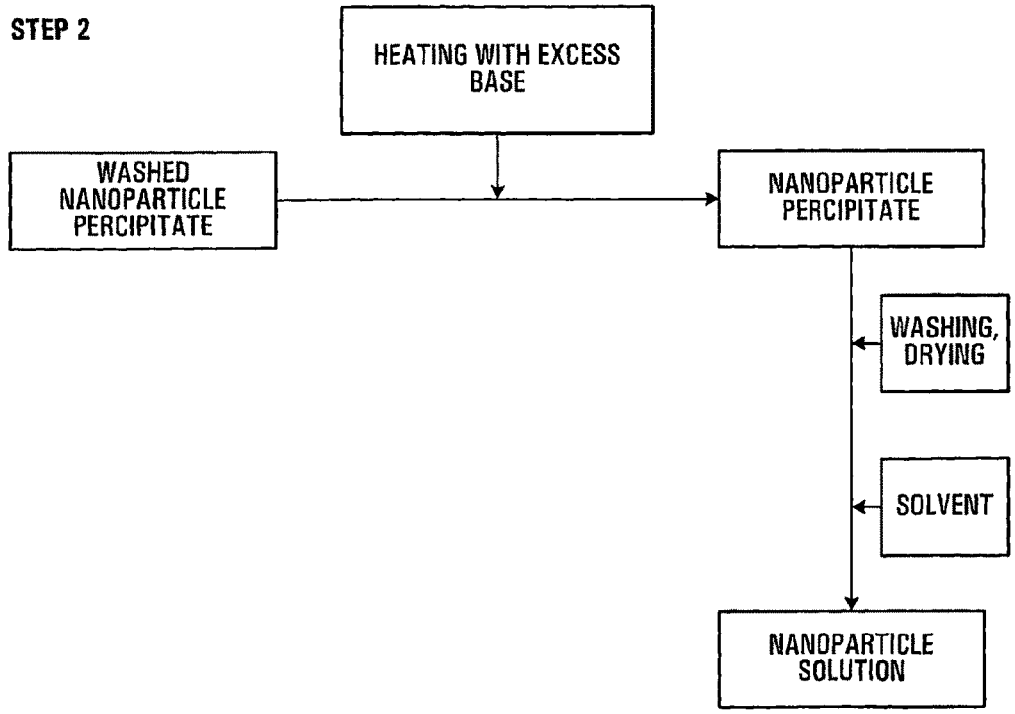
Figure 2:
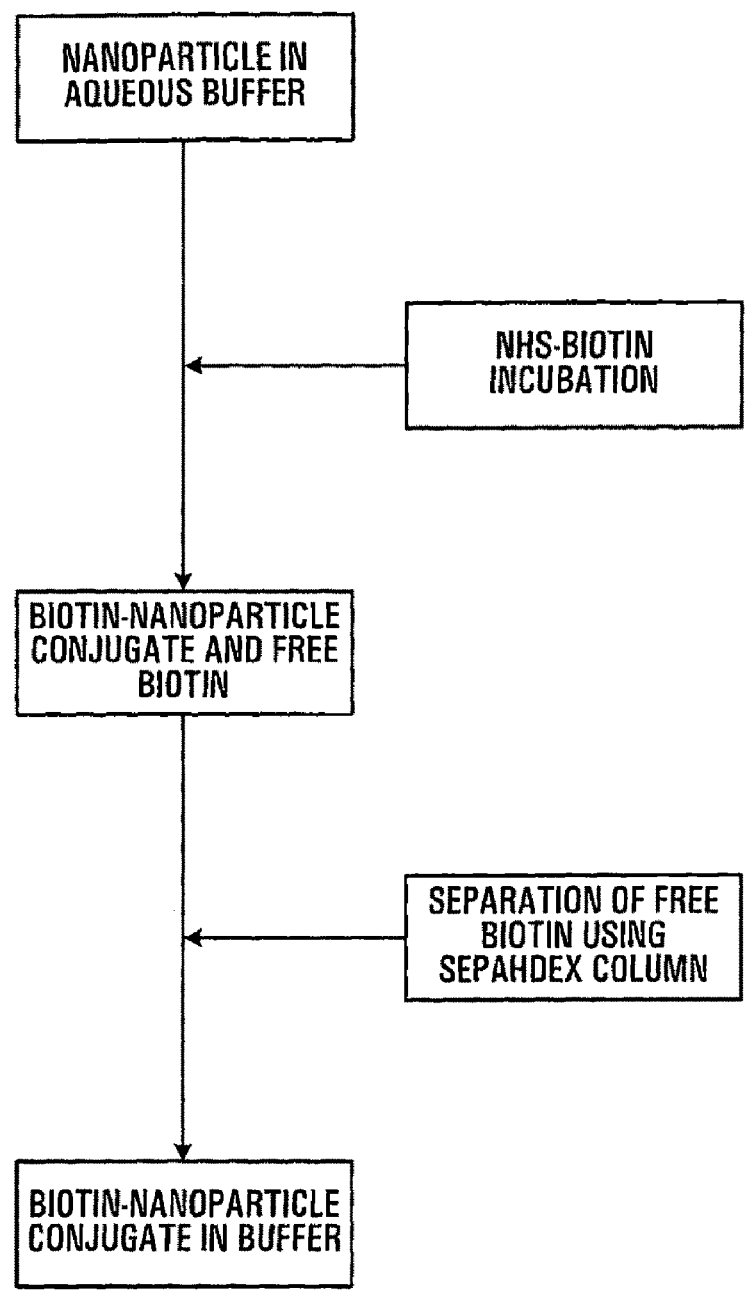
FIG. 2 is a flow chart illustrating a process for biotinylating amine- and phosphonate-functionalized nanoparticle surfaces.
Figure 4:
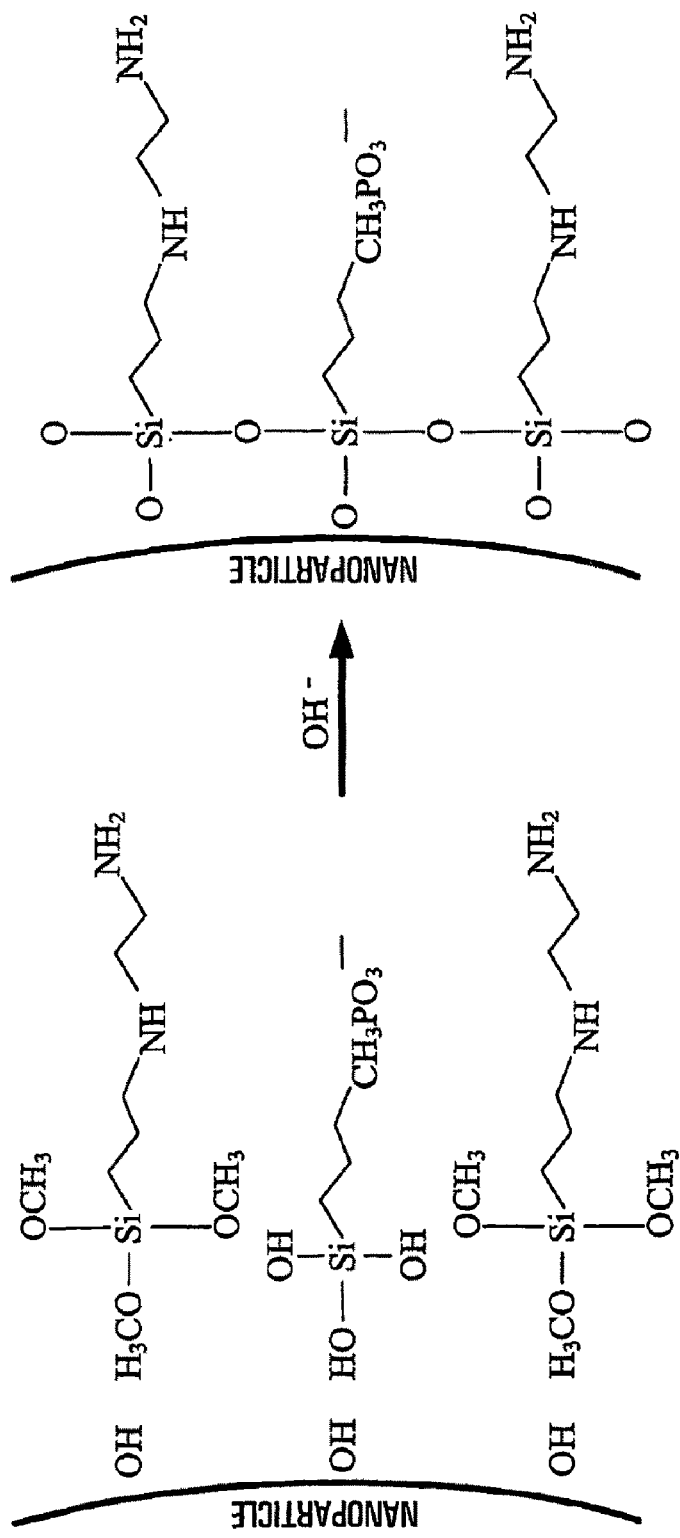
FIG. 4 shows a reaction scheme of silane conjugation on a hydroxide-terminated oxide nanoparticle surface.
Figure 5:
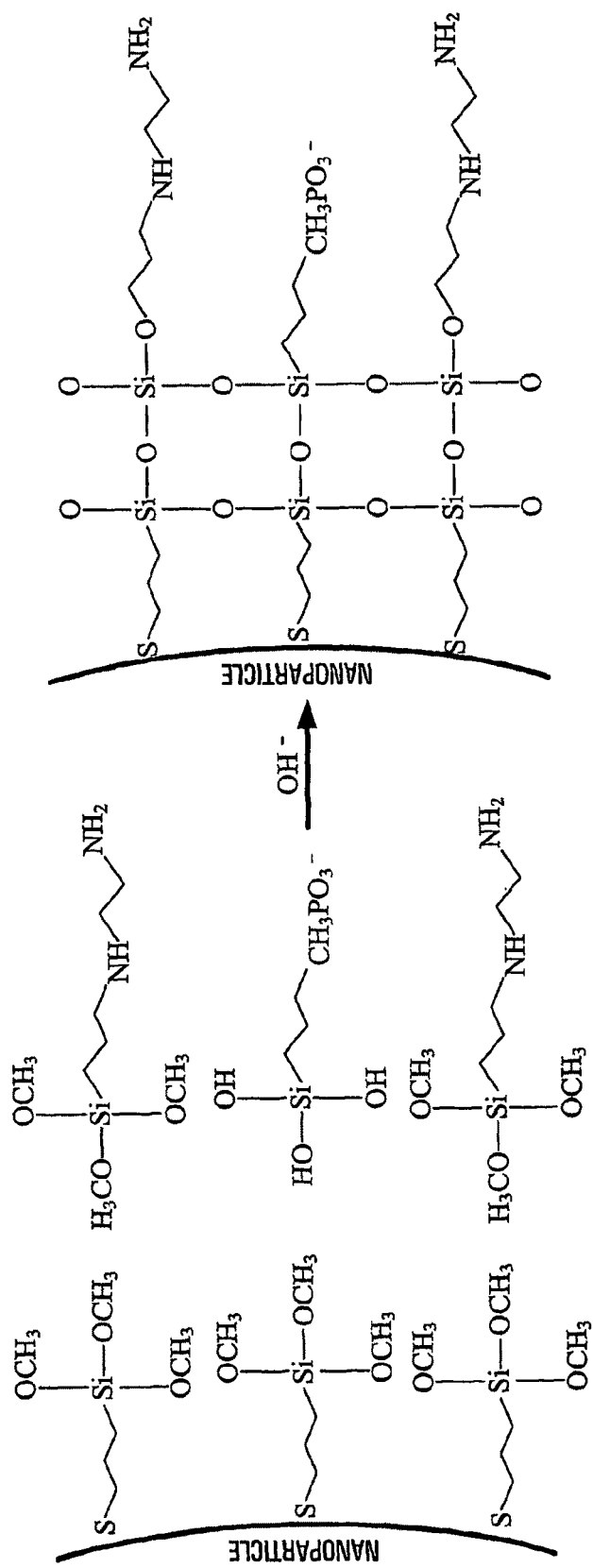
FIG. 5 shows a reaction scheme of silane conjugation chemistry on a metal nanoparticle surface via a linker mercaptosilane.

This invention discloses a two-step silanization method to derive soluble nanoparticles with different types of surface functionality.

In previous attempts to silanize nanoparticle surfaces, results were difficult to reproduce and nanoparticle aggregates were often obtained. In practice, most covalent bridging schemes for nanoparticle surfaces have this aggregation problem due to competitive interparticle bridging processes. This detrimental process was further complicated with silanization reactions, as silane groups are sensitive to reaction conditions such as moisture, solvents and residual silanol, which induce particle-particle aggregation. This problem is solved herein by performing the silanization reaction in non-aqueous media via a two-step process. In some embodiments, the silanized nanoparticles obtained are completely soluble in aqueous solvents, and they remain stable for long periods of time. Bioconjugates, such as biotinylated nanoparticles, can be prepared using these surface-functionalized nanoparticles, and these bioconjugates are also stable and soluble. The method described herein is general, efficient and highly reproducible when compared to previous methods.

In order to avoid the interparticle reactions that lead to aggregation of nanoparticles, the process according to the present invention proceeds in a two-step manner, which provides some control on the silazination reactions.

In a first step, a nanoparticle is reacted with a functionalized silane in the presence of a controlled amount of base such that the functionalized silane undergoes substantially only a single hydrolysis reaction. As such, the functionalized silane forms a single bond with the nanoparticle to obtain a partially conjugated silanated nanoparticle. The degree and rate of silane conjugation can be controlled by varying the temperature and the amount of base in the reaction system. In some embodiments where a hydroxide base is used, the ratio of functionalized silane to base is about 1:1. In other embodiments where a non-hydroxide base is used, the ratio of functionalized silane to base can be less than 1.

In some embodiments, the base used in the first step is soluble in organic solvents. Examples of suitable bases include hydroxide bases, such as tetra-methyl ammonium hydroxide, tetra-butyl ammonium hydroxide, or sodium hydroxide, and non-hydroxide bases such as an alkyl amine. Examples of suitable alkyl amines include $C_1$-$C_{16}$ alkyl amines and $C_1$-$C_6$ alkyl amines. For certain alkyl amines, the silanization reaction can be fairly slow, although the reaction rate can be increased by heating. Water can also help silanization, as it can provide hydroxide groups to the system. The presence of small amounts of water can perform silanization without any other bases. In some embodiments, small amounts of water can come from organic solvents.

The silane conjugation in the first step is preferably performed in an organic solvent and substantially in the absence of water. Examples of suitable solvents include organic-like alcohols, hydrocarbons, and benzene derivatives. Specific examples of suitable solvents include toluene, cyclohexane, methanol, ethanol, mixtures of ethanol and toluene, DMSO, DMF, and liquid ammonia. Toluene is a preferred solvent for this step, as partially conjugated silanated nanoparticle precipitate once formed so that unbound silane molecules can be removed. Preferably, the partially conjugated nanoparticle intermediate is somewhat insoluble in the solvent used, which aids in the separation of the intermediate. The removal of unbound silanes is preferred at this point, as free silanes give rise to thick silica shells and/or interparticle silanization in the second step of the reaction. Removal of unbound silanes can be assisted by the addition of solvents that induce the precipitation of silane bound particles.

In the second step of the reaction, the intermediate isolated from the first step is placed in a solvent in which it is substantially insoluble, where it is then reacted with an excess of a base that is soluble in the solvent, to complete the intraparticle silanization of the functionalized silane moieties. Examples of suitable bases for the second reaction step include hydroxide bases, such as tetra-methyl ammonium hydroxide and tetra-butyl ammonium hydroxide, and non-hydroxide bases such as an alkyl amine. Again, Examples of suitable alkyl amines include $C_1$-$C_{16}$ alkyl amines and $C_1$-$C_6$ alkyl amines.

Examples of suitable solvents for the second step include organic-like alcohols, hydrocarbons, and benzene derivatives. Specific examples of suitable solvents include toluene, cyclohexane, methanol, ethanol, mixtures of ethanol and toluene, DMSO and DMF. As the partially conjugated silanated nanoparticle is substantially insoluble in the solvent used in the second step, there is minimal contact between each nanoparticle, greatly diminishing the amount of interparticle reactions and substantially avoiding the productions of nanoparticle aggregates.

Control experiments were carried out to determine the effectiveness of the process described herein. In some of these control experiments, where the second step was omitted, it was found that the nanoparticles were highly soluble, but they would slowly precipitate with time and that complete precipitation would occur after several hours or days.

In another embodiment, the residual silanol/alkoxysilane in the partially conjugated silanated nanoparticles formed in step (a) are rendered unreactive, for example by conversion to alkylsilane groups. This can be achieved, for example, by reacting the partially conjugated silanated nanoparticles with a chlorosilane, examples of which include chlorotrialkyl silanes such as chlorotrimethyl silane. As the silanol/alkoxysilane are rendered unreactive, inter particle coupling via these groups can be blocked.

Silanes

The process of the present invention can be carried out with various types of silanes. In one embodiment, the silanes comprise a silyl group substituted by 1, 2 or 3 $C_1$-$C_6$ alkoxy groups or silanol groups. Examples of suitable silanes are shown in FIG. 3. In FIG. 3, the silanes have trimethoxy silyl, methoxy silyl, or silanol groups at one end, which groups can hydrolyze in a basic medium to form a silica shell around a nanoparticle. The silanes also have organic functional groups, examples of which include phosphonate groups, amine groups, thiol groups, $C_1$-$C_{20}$ alkyl, $C_1$-$C_{20}$ alkene, $C_1$-$C_{20}$ alkyne, azido groups, or epoxy groups. These groups can be found on the functionalized silanes prior to the first step of the reaction, or they can be added to the silane groups after they have been conjugated with the nanoparticle. Silanes with phosphonate functional groups can render the nanoparticles water-soluble. Silanes with amine functional groups are useful for bioconjugation via amide bond formation, and they render nanoparticles water-soluble, but only at acidic pH. Silanes with thiol groups can be used for bioconjugation via disulfide bond formation. Mercaptosilanes can be used as linker molecules for preparing silane/silica coatings on metallic nanoparticles, and such mercaptosilane bearing nanoparticles show increased solubility in alcohols. Silanes terminated with long hydrophobic chains can be used to render nanoparticles more hydrophobic, and therefore more soluble in organic solvents such as toluene. When preparing functionalized nanoparticles, a single type of silane or a mixture of silanes can be employed. As such, nanoparticles that are water-soluble and stable over a wide range of pH, as well as reactive to biological molecules, can be obtained, for example, by using a mixture of phosphonate silanes and aminosilanes.

Nanoparticles

The nanoparticles used in the present invention are preferably metal oxides, semiconductors or metallic nanoparticles. In some embodiments, the nanoparticles used to prepare the surface-functionalized nanoparticle are near-monodisperse, and they can comprise, for example, iron oxide, zinc oxide, manganese oxide, nickel oxide or chromium oxide, cadmium-selenium (CdSe), silver or gold. In some embodiments, the nanoparticles have a diameter or from about 2 to about 50 nm, while in other embodiments, their diameter: is from about 2 to about 20 nm. In further embodiments, the nanoparticles can have diameters of from about 2 to about 3 nanometers.

While silanization of compounds such as iron oxide and zinc oxide can be carried out without using any linker silane, silanization of gold, silver and CdSe nanoparticles can involve a linker silane, such as mercaptosilane. When metal oxides are present in the nanoparticle, the presence of a base, for example tetra-methyl ammonium hydroxide, forms hydroxide-terminated nanoparticles which can react with functionalized silanes. When a non-oxide nanoparticle is used, an additional reaction step may be carried out where a linker silane is attached to the nanoparticle to provide a reactive group on the surface of the nanoparticle. An example of a suitable linker silane is mercaptosilane, which chemisorbs on the surface of metallic nanoparticles. The reaction of mercaptosilane with the nanoparticles can be carried out prior to the first step of the reaction. Alternatively, this reaction can be carried out at the same time as the first step.

In most nanoparticle synthesis, excess surfactants and ligands are used. In such cases, the nanoparticles are separated from the free ligands to insure that the silanization reaction in the first step leads to products that are partially or completely insoluble. This is particularly important when no linker silanes are used, for example in the cases of the functionalization of nanoparticles comprising iron oxide or zinc oxide. Free ligands can be removed, for example, via multiple precipitations in methanol.

Bioconjugation

Once water-soluble functionalized nanoparticles are prepared, they can be conjugated with biological molecules. Examples of suitable biological molecules include, for example, biotin, low molecular weight sugars such as Dextran, short peptides, single strand DNA, or Concanvalin A. The surface-functionalized nanoparticle and the biological molecules can be conjugated, for example, through an amide, a disulfide or an ester bond.

Figure 9A:
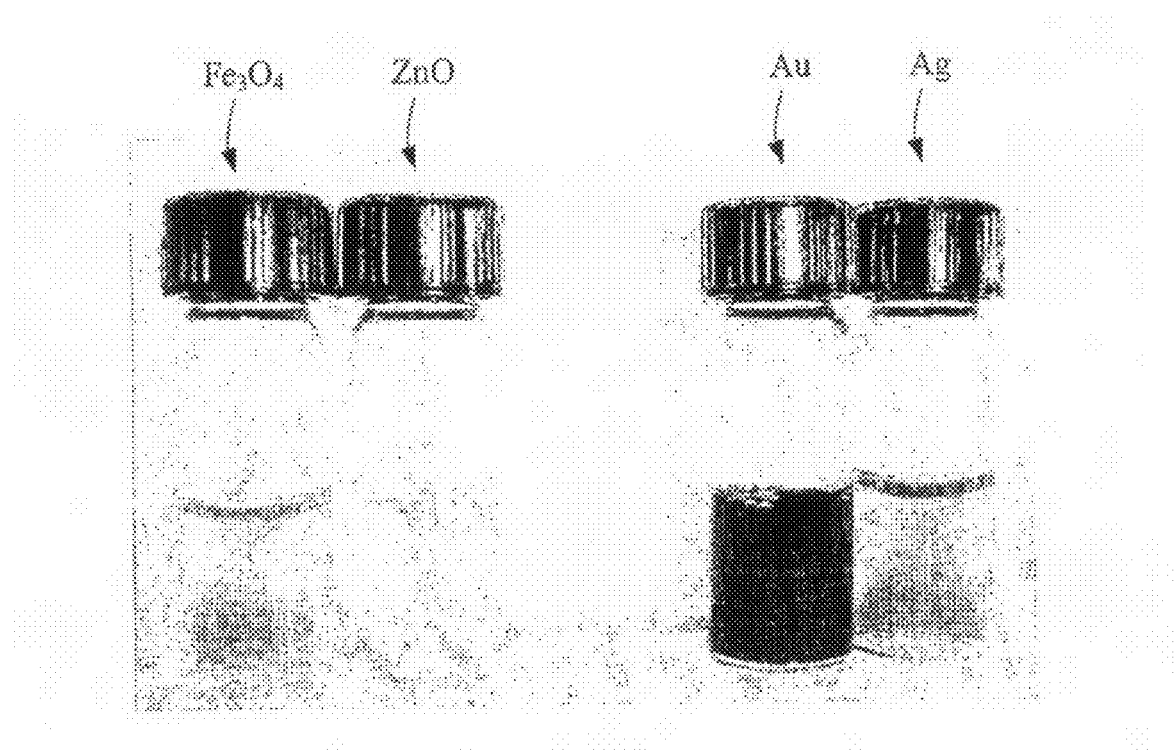
FIG. 9 shows optically clear aqueous solutions of various silanized nanoparticles under (a) visible and (b) ultraviolet light.
Figure 9B:
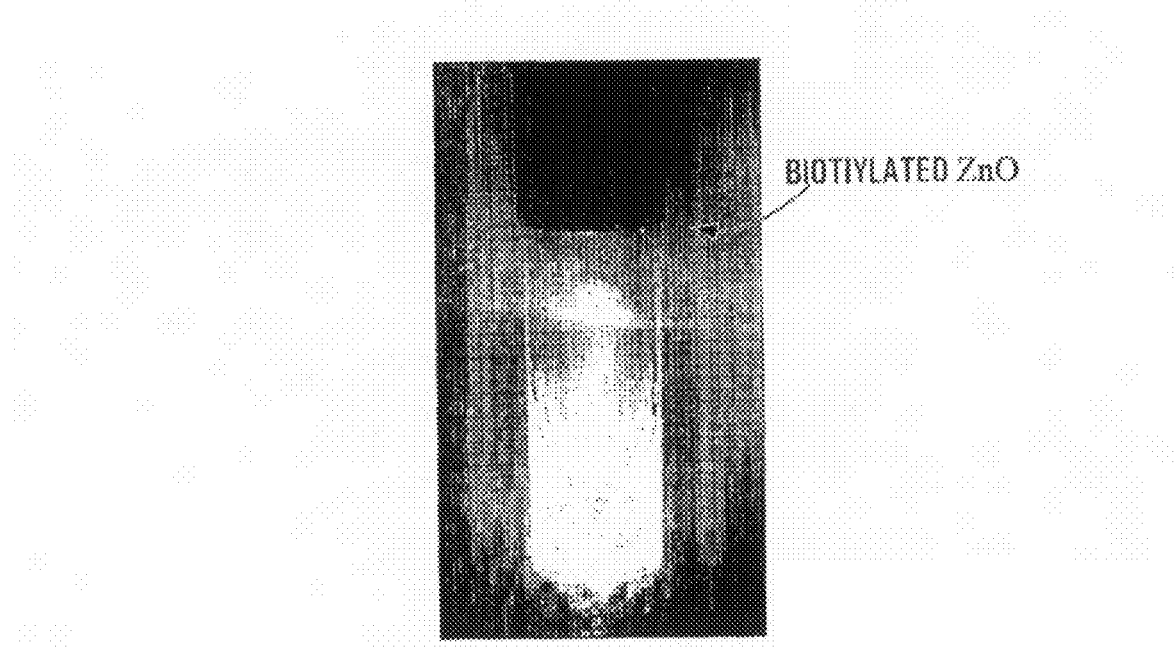

An example of such bioconjugation is the biotinylation of nanoparticles, which process can be carried out in a simple one-step mechanism. Biotinylation of nanoparticles is important for selective targeting of biologically active substance via biotin-avidin interaction. Earlier results in the art show that biotinylated particles often aggregate due to excessive biotin loading per particle. With the functionalized nanoparticles of the present invention, the biotinylated particles can remain stable and soluble as the presence of phosphonate groups provides increased water-solubility. FIG. 9b shows the fluorescence property of a biotinylated zinc oxide nanoparticle solution.

The process of the present invention also provides some control on the number of biological molecules attached to each nanoparticle, by controlling the amount of functionalized silane groups that bear the required reactive functionality to bind with the biomolecules (such as amine or thio groups). In some embodiments, the combination of amine and phosphonate groups has proven to be useful for bioconjugation, as the bioconjugated particles show good water-solubility characteristics and the number of biomolecules of the particle surface can be controlled.

EXAMPLES

The following examples are provided to illustrate the invention. It will be understood, however, that the specific details given in each example have been selected for purpose of illustration and are not to be construed as limiting the scope of the invention. Generally, the experiments were conducted under similar conditions unless noted.

General Procedures for Nanoparticle Preparation

Near-monodisperse gold and silver nanoparticles in the size range of 2-20 nm were prepared in toluene according to standard procedure (Jana et al., J. Am. Chem. Soc. (2003) 125, 14280). Metal salts were dissolved in toluene in the presence of long-chain tetra-alkyl ammonium salts, amines or acids, and then reduced using a mixture of weak and strong reducing agents. Strong reducing agents induce particle nucleation and weak reducing agents promote particle growth. By varying the ratio of the two reducing agents, particle size can be controlled.

Near-monodisperse iron oxide nanoparticles were prepared according to a known procedures (Jana et al., Chem. Mater (2004) 16, 3931-3935). Long-chain carboxylic acid salts of iron(II) were heated in the presence of the respective carboxylic acid in octadecene at 300° C. Particle size was controlled between 8 nm and 40 nm by varying the amount of free carboxylic acid. Particles of 2-5 nm were prepared under similar conditions with octadecylamine as the additional capping agent.

Zinc oxide nanoparticles were prepared using a modified literature approach (Meulenkamp et al., J. Phys. Chem. B (1998) 102, 5566; Abdullah et al., Adv. Func. Mater. (2003) 13, 800). To a boiling ethanol solution of zinc acetate and long-chain carboxylic acids, a boiling ethanol solution of tetra-methyl ammonium hydroxide was injected. The zinc oxide nanoparticles started to grow within minutes and the reaction was stopped by rapidly quenching the reaction temperature. Following this approach, monodisperse particles of 5-10 nm were prepared, depending on growth duration.

General Procedures for Silane Conjugation

All silane solutions were prepared in toluene (100 mM) except for phosphonate silane, which was prepared in methanol. Fresh stock solutions were prepared daily, as silanes are reactive to moisture. Tetra-methyl ammonium hydroxide solution (100 mM) was prepared in methanol. Optically clear nanoparticle solutions were prepared in toluene for all silane conjugation experiments. Iron oxide and zinc oxide nanoparticles were purified from free ligands, using standard precipitation-redispersion protocol, prior to preparing their toluene solution.

In the silanization experiments, either individual silane or mixtures of silanes were used. In most of the mixed silane experiments, phosphonate silane and aminosilane were used and their molar ratio was varied from about 1:100 to about 100:1. In the silanization of metallic nanoparticles, mercaptosilane (linker silane) and other silane mixtures were used. In the first step of silane conjugation, 4-5 mL of nanoparticle solution was mixed with a silane solution, and in specific cases, mixed with an equivalent amount (with respect to total silanes) of tetra-methyl ammonium hydroxide solution. The mixture was heated to 60° C. for 15-30 minutes for iron oxide and zinc oxide. For gold and silver, the mixture was either stirred for a long time (4-5 hr) or heated to 60° C. Precipitation was observed in most cases, with a clear supernatant. When there was partial precipitation or no precipitation, minimum methanol was added for complete precipitation. The precipitate was separated from the supernatant, and washed with methanol/toluene.

In the second step of conjugation, the solid precipitate was mixed with toluene and tetra-methyl ammonium hydroxide solution, and then heated (for oxides) or stirred for 30-60 minutes. Intraparticle silane conjugation took place in this step.

The solid precipitate was finally washed repeatedly in toluene and/or methanol to remove free silanes and bases. Particles can be prepared from milligram to gram scale with this approach. Finally, particles were dispersed in water, aqueous buffer or organic solvent. All the solutions were optically clear, and the particle concentration could be varied from μg/mL to mg/mL.

General Procedures for Bioconjugation

In order to show that the surface-functionalized nanoparticles of the invention are useful for bioconjugation, biotinylated particles were prepared using commercially available activated biotin. The carboxylic acid group in biotin was activated with n-hydroxy succinamide (NHS) to react with primary amines. Amine-phosphonate bifunctionalized nanoparticles were used for bioconjugation. In a typical experiment, the dimethylformamide solution of activated biotin was mixed with the particle solution in phosphate buffer and stirred for 12 hr. After biotinylation, free biotin was separated using a Sephadex column.

Example 1

Preparation of Amine-Functionalized 5-nm $Fe_3O_4$ Nanoparticles Using Aminosilane Iron oxide nanoparticles of 5 nm were prepared in octadecene using a mixture of octadecylamine and iron(II) stearate. After preparation, the nanoparticles were purified via methanol precipitation and toluene redispersion. The toluene dispersion was then used in two-step silanization with aminopropyl trimethoxysilane at 60° C. Final solid nanoparticles were dispersed in water using dilute formic/acetic acid. The nanoparticles were partially soluble in water without acid.

Figures 6A, 6B:
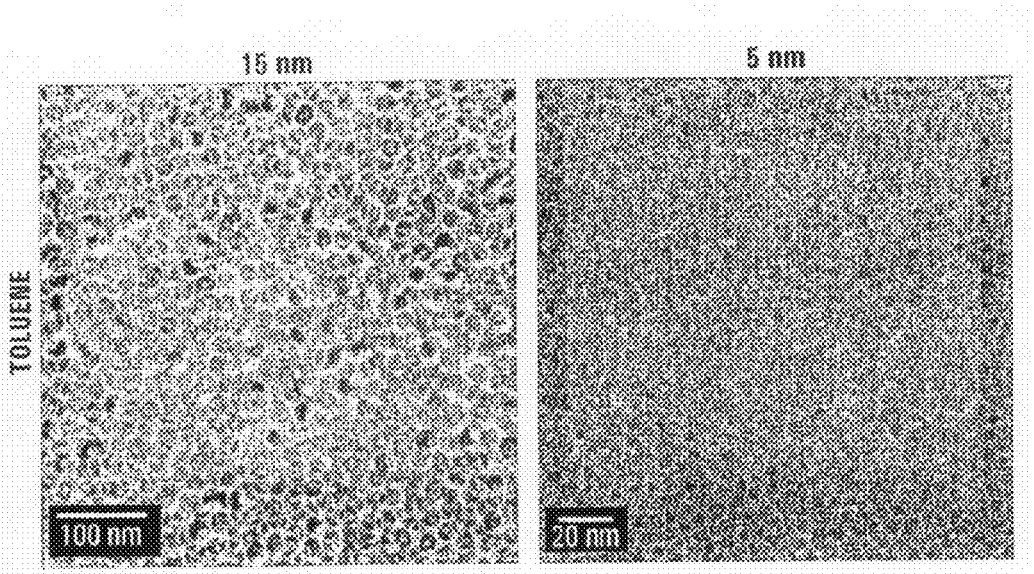
FIG. 6 shows a transmission electron microscopy (TEM) of iron oxide nanoparticles of two different sizes before and after silane coating.
Figures 6C, 6D:
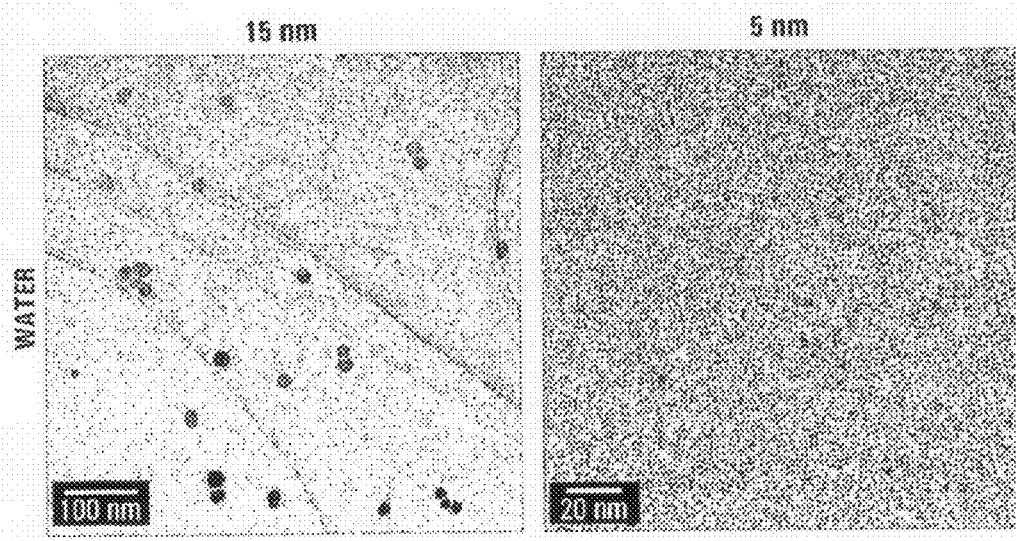

TEM images of 5-nm oxide nanoparticles, before and after silanization, are shown in FIG. 6. From the TEM images, it can be seen that particle size does not change substantially during silanization, that the silane coating is too thin to be seen, and that the particles are isolated after being coated.

Example 2

Preparation of Amine- and Phosphonate-Bifunctionalized 15-nm $Fe_3O_4$ Nanoparticles Using Mixed Silanes Iron oxide nanoparticles of 15 nm were prepared in octadecene using a mixture of iron(II) oleate and oleic acid. After preparation, the nanoparticles were purified via methanol precipitation and toluene redispersion. The toluene dispersion was then used in two-step silanization with a mixture of phosphonate silane and bis(aminoethyl)aminopropyl trimethoxysilane at 60° C. Final solid nanoparticles were dispersed in water using dilute formic/acetic acid.

TEM images of 15-nm oxide nanoparticles, before and after silanization, are shown in FIG. 6. Again, the TEM images support the earlier observations that particle size does not change substantially during silanization, that the silane coating is too thin to be seen, and that the particles are isolated after being coated.

Example 3

Preparation of Hydrophobic 5-nm $Fe_3O_4$ Nanoparticles Using Octadecylsilane

Iron oxide nanoparticles of 5 nm were prepared as described in Example 1. The purified nanoparticles were dispersed in toluene and used in two-step silanization with hexadecyl trimethoxysilane at 60° C. The silanized nanoparticles were dispersed in toluene/hexane.

Example 4

Preparation of Amine-Phosphonate-Bifunctionalized 8-nm ZnO Nanoparticles Using Mixed Silanes Zinc oxide nanoparticles of 8 nm were prepared in ethanol using zinc(II) acetate as precursor and oleic acid as particle stabilizer. They were purified from free ligands via centrifuging, and were redispersed in toluene. The optically clear toluene dispersion was used for two-step silanization with a mixture of bis(aminoethyl)aminopropyl trimethoxysilane and phosphonate silane at 60° C. The silanized nanoparticles were dispersed in an aqueous buffer.

Example 5

Preparation of Amine-Functionalized 2-nm Ag Nanoparticles Using Aminosilane

Silver nanoparticles of 2 nm were prepared in toluene using silver(I) acetate as precursor, decanoic acid-dodecylamine as ligand, and tetrabutyl ammonium borohydride as reducing agent. The as-prepared nanoparticle solutions were used directly for silanization. The optically clear toluene dispersion was treated with a base and a linker silane, bis(aminoethyl)aminopropyl trimethoxysilane and stirred for 4-5 hr without heating so as to prevent particle growth. Particles were centrifuged and separated from free ligands and treated with excess base for 4-5 hr. The silanized nanoparticles were dispersed in an aqueous buffer using a small amount of organic acid.

Example 6

Preparation of Amine-Phosphonate-Bifunctionalized 10-nm Ag Nanoparticles Using Mixed Silanes Silver nanoparticles of 10 nm were prepared in toluene using silver(I) acetate as precursor, decanoic acid-dodecylamine as ligand, and a mixture of tetrabutyl ammonium borohydride and hydrazine as reducing agents. The as-prepared nanoparticle solution was used directly for silanization. The optically clear toluene dispersion was mixed with a linker silane, methoxydimethylaminopropyl silane, phosphonate silane and a base, and stirred for 4-5 hr without heating. The nanoparticles were centrifuged and separated from free ligands, and treated with excess base for 4-5 hr. The silanized nanoparticles were isolated and dispersed in an aqueous buffer.

Example 7

Preparation of Amine-Functionalized 8-nm Au Nanoparticles Using Mixed Silanes

Gold nanoparticles of 8 nm were prepared in toluene using gold (III) chloride-didodecyldimethylammonium bromide as precursor, decanoic acid as ligand, and tetrabutyl ammonium borohydride as reducing agent. As prepared nanoparticle solution was used directly for silanization. The optically clear toluene dispersion was mixed with linker silane and bis(aminoethyl)aminopropyl trimethoxysilane, and heated to 60° C. for 30 min. Particles were centrifuged and separated from free ligands, and again heated with excess base for another 30 min. Solid nanoparticles were isolated and dispersed in water using a small amount of organic acid.

Figures 7A, 7B:
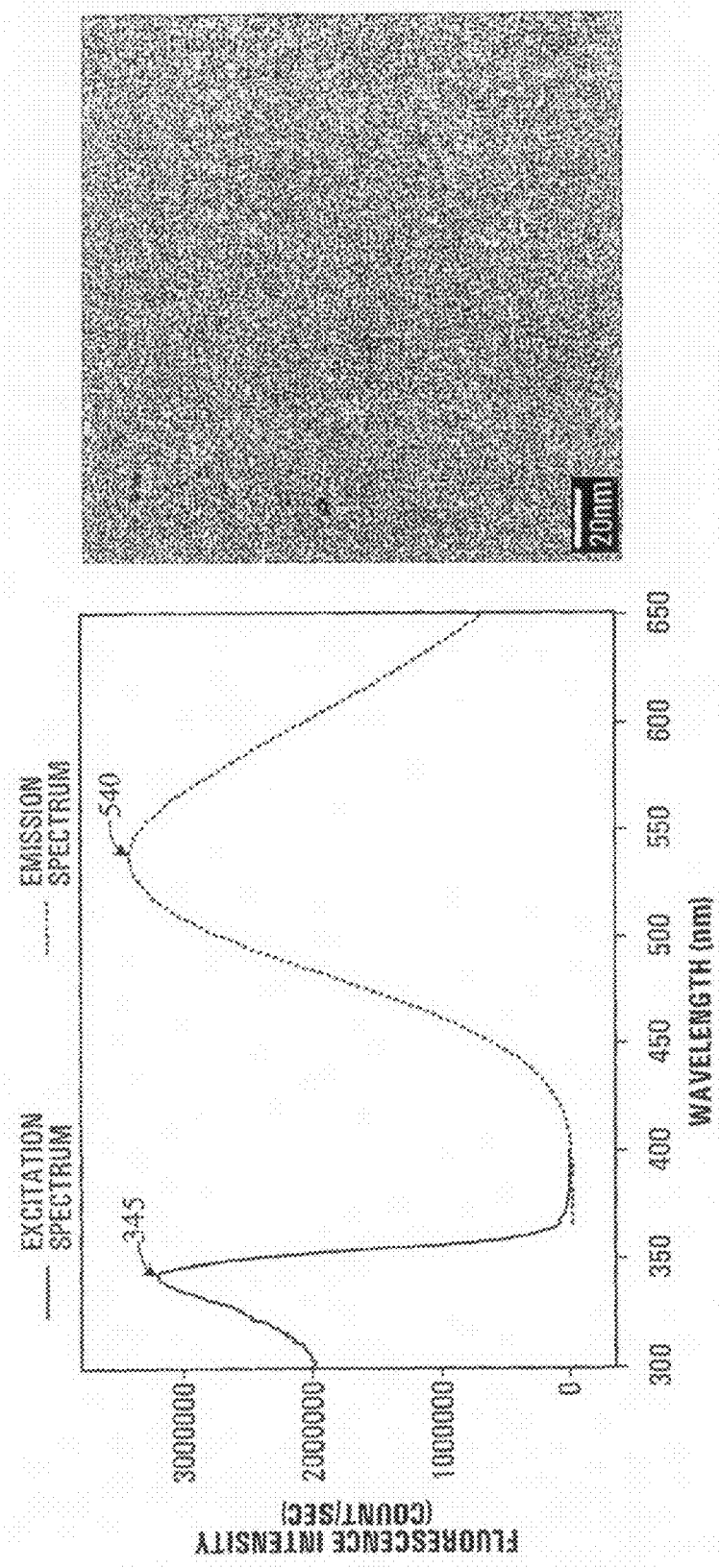
FIG. 7 shows an excitation and emission spectra (a) and a TEM micrograph (b) of biotinylated ZnO nanoparticles.

An UV-visible absorption spectra and a TEM micrograph of silanized gold and silver nanoparticles in aqueous buffer are shown in FIG. 7. Again, this figure shows that the silane coating is too thin to be seen, and that the particles are isolated after silane coating.

Example 8

Biotinylation of Amine-Phosphonate-Bifunctionalized 8-nm ZnO Nanoparticles

ZnO nanoparticles modified with phosphonate silane and aminosilane were prepared in a phosphate buffer. Dimethylformamide solution of activated biotin (NHS-biotin) was mixed and stirred for 12 hr and then passed through a Sephadex G-25 column three times for separation of free biotin. The optically clear biotinylated nanoparticles were preserved at 4° C.

Figure 8:
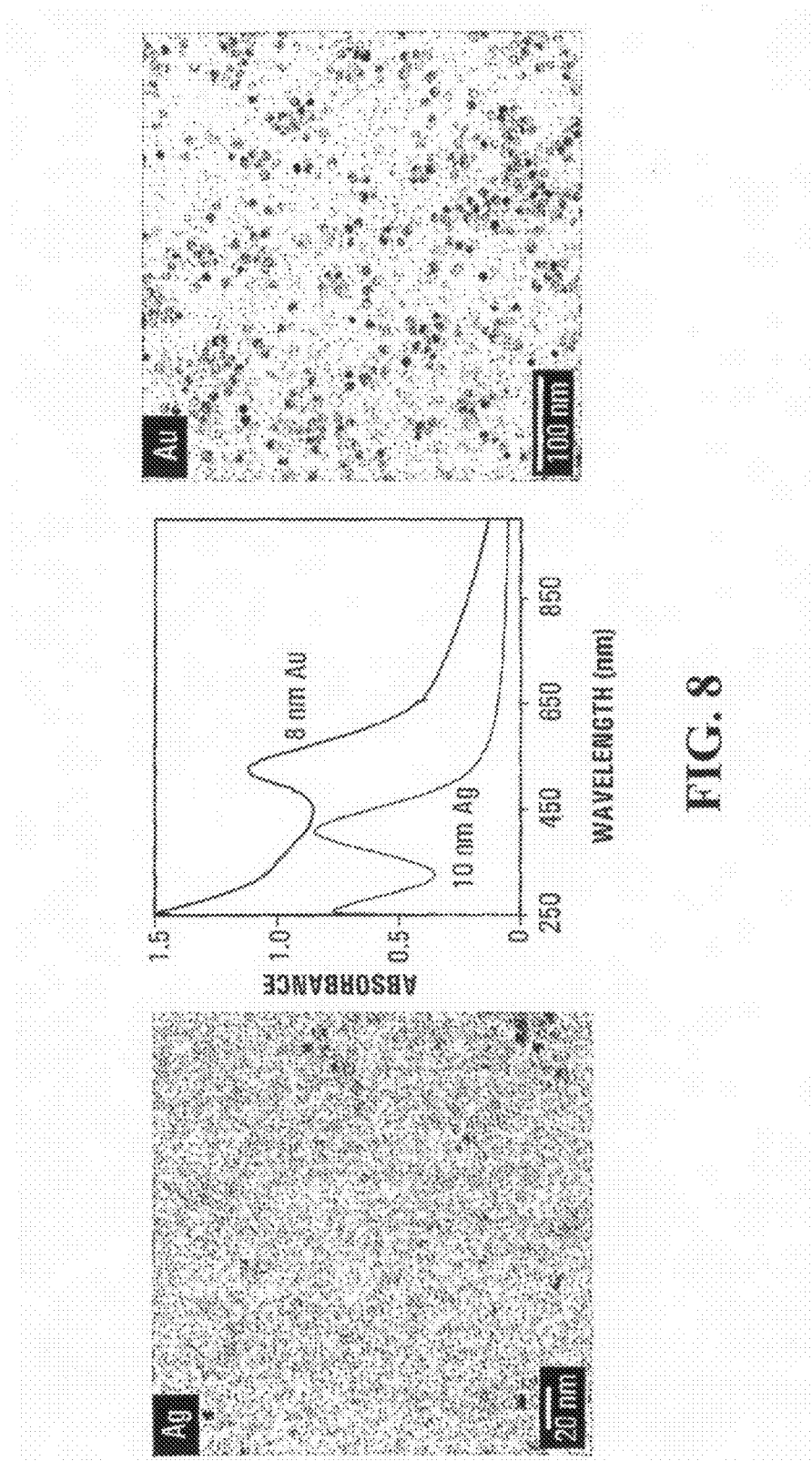
FIG. 8 shows a UV-visible absorption spectra and TEM of silanized gold and silver nanoparticles in aqueous buffer.

An excitation and emission spectra and a TEM micrograph of biotinylated ZnO nanoparticles are shown in FIG. 8. It is seen from this figure that the biotinylated particles are isolated and fluorescent.

All publications, patents and patent applications cited in this specification are herein incorporated by reference as if each individual publication, patent or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a", "an", and "the" include plural reference unless the context clearly dictates otherwise. Unless defined otherwise all technical and scientific terms used herein have the same meaning as commonly understood to one of ordinary skill in the art to which this invention belongs.

The invention claimed is:

1. A process for the preparation of a surface-functionalized nanoparticle comprising:
   (a) reacting a nanoparticle with a functionalized silane and a base in a non-aqueous solvent to obtain a partially conjugated silanated nanoparticle, wherein the functionalized silane and the base are present in a molar ratio of about 1:1 or less;
   (b) separating the partially conjugated silanated nanoparticle formed in step (a);
   (c) reacting the partially conjugated silanated nanoparticle from step (b) with a base in a solvent in which the partially conjugated silanated nanoparticle is insoluble and in which the base is soluble.

2. A process according to claim 1, wherein the nanoparticle comprises a metal oxide.

3. A process according to claim 1, wherein the nanoparticle comprises zinc oxide, iron oxide, manganese oxide, nickel oxide or chromium oxide.

4. A process according to claim 1, wherein prior to, or during, step (a) the nanoparticle is reacted with a mercaptosilane to obtain a mercaptosilane-functionalized nanoparticle.

5. A process according to claim 4, wherein the nanoparticle is metallic.

6. A process according to claim 4, wherein the nanoparticle comprises gold, silver or CdSe.

7. A process according to claim 1, wherein the nanoparticle has a diameter of from 2 to 50 nm.

8. A process according to claim 1, wherein the functionalized silane comprises a silyl group substituted by 1, 2 or 3 $C_1$-$C_6$ alkoxy groups or silanol groups.

9. A process according to claim 1, wherein the functionalized silane comprises a trimethoxy silyl group, a methoxy silyl group, an ethoxy silyl group or a silanol group.

10. A process according to claim 1, wherein the functionalized silane comprises a phosphonate group, an amine group, a thiol group, a $C_1$-$C_{20}$ alkyl, a $C_1$-$C_{20}$ alkene, a $C_1$-$C_{20}$ alkyne, an azido group, or an epoxy group.

11. A process according to claim 1, wherein the base in step (a) is a hydroxide base.

12. A process according to claim 1, wherein the base in step (a) is a non-hydroxide base.

13. A process according to claim 1, wherein the base in step (a) is tetra-methyl ammonium hydroxide, tetra-butyl ammonium hydroxide, sodium hydroxide or an alkyl amine.

14. A process according to claim 1, wherein the base is a hydroxide base, and the functionalized silane and the hydroxide base are present in a molar ratio of about 1:1.

15. A process according to claim 1, wherein the base is a non-hydroxide base, and the functionalized silane and the non-hydroxide base are present in a molar ratio less than 1.

16. A process according to claim 1, wherein the non-aqueous solvent is selected from the group consisting of hydrocarbons and benzene derivatives.

17. A process according to claim 1, wherein the non-aqueous solvent is selected from the group consisting of toluene, cyclohexane, methanol, ethanol, mixtures of ethanol and toluene, DMSO, DMF, and liquid ammonia.

18. A process according to claim 1, wherein the non-aqueous solvent is toluene.

19. A process according to claim 1, wherein the base in step (b) is a hydroxide base.

20. A process according to claim 1, wherein the base in step (b) is a non-hydroxide base.

21. A process according to claim 1, wherein the base in step (b) is tetra-methyl ammonium hydroxide, tetra-butyl ammonium hydroxide or an alkyl amine.

22. A process according to claim 1, wherein the solvent in step (b) is selected from the group consisting of hydrocarbons and benzene derivatives.

23. A process according to claim 1, wherein the solvent in step (b) is selected from the group consisting of toluene, cyclohexane, methanol, ethanol, mixtures of ethanol and toluene, DMSO, and DMF.

24. A process according to claim 1, wherein the solvent in step (b) is toluene.

25. A process for the preparation of a surface-functionalized nanoparticle comprising:
   (a) reacting a nanoparticle with a functionalized silane and a base in a substantially non-aqueous solvent to obtain a partially conjugated silanated nanoparticle, wherein the functionalized silane and the base are present in a molar ratio of about 1:1 or less;
   (b) separating the partially conjugated silanated nanoparticle formed in step (a);
   (c) reacting the partially conjugated silanated nanoparticle from step (b) with a chlorosilane.

* * * * *